(12) United States Patent  (10) Patent No.: US 8,761,508 B2
Kimura et al.  (45) Date of Patent: Jun. 24, 2014

(54) IMAGE PROCESSING SYSTEM, IMAGE PROCESSING APPARATUS AND COMPUTER READABLE MEDIUM

(75) Inventors: Tetsuya Kimura, Kanagawa (JP); Kensuke Ito, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 545 days.

(21) Appl. No.: 13/094,440

(22) Filed: Apr. 26, 2011

(65) Prior Publication Data

US 2012/0128247 A1 May 24, 2012

(30) Foreign Application Priority Data

Nov. 18, 2010 (JP) ................................ 2010-257515

(51) Int. Cl.
 *G06K 9/34* (2006.01)
(52) U.S. Cl.
 USPC .......................................... 382/173; 382/176
(58) Field of Classification Search
 None
 See application file for complete search history.

(56) References Cited

U.S. PATENT DOCUMENTS

| | | | | |
|---|---|---|---|---|
| 7,769,212 | B2 * | 8/2010 | Hwang et al. | 382/124 |
| 8,586,928 | B2 * | 11/2013 | Sinbar et al. | 250/340 |
| 2005/0063562 | A1 * | 3/2005 | Brunk et al. | 382/124 |
| 2007/0183633 | A1 * | 8/2007 | Hoffmann | 382/116 |
| 2008/0019578 | A1 * | 1/2008 | Saito et al. | 382/124 |
| 2008/0294900 | A1 | 11/2008 | Cowburn | |

FOREIGN PATENT DOCUMENTS

| | | | |
|---|---|---|---|
| JP | 2004-153405 | A | 5/2004 |
| JP | 2006-164180 | A | 6/2006 |
| JP | 2008-509498 | A | 3/2008 |
| JP | 4103826 | B2 | 4/2008 |

OTHER PUBLICATIONS

NPL—3M.com, "3M Tegaderm Transparent Dressing" product brochure. [Product is available for public purchase since 1997.], 1 page.*

* cited by examiner

*Primary Examiner* — Chan Park
*Assistant Examiner* — Ha Le
(74) *Attorney, Agent, or Firm* — Sughrue Mion, PLLC

(57) ABSTRACT

An image processing system includes a first image processing apparatus and a second image processing apparatus. The first image processing apparatus includes a first image obtaining module, a first image extraction module, a first density extraction module, a first feature conversion module, a register module. The first image obtaining module obtains an image of an object having a seal impressed on a face thereof and having a film formed or laminated on the face thereof. The second image processing apparatus includes a second image obtaining module, a second image extraction module, a second density extraction module, a second feature conversion module, and a collation module.

12 Claims, 16 Drawing Sheets

*FIG. 9A*  *FIG. 9B*  *FIG. 9C*
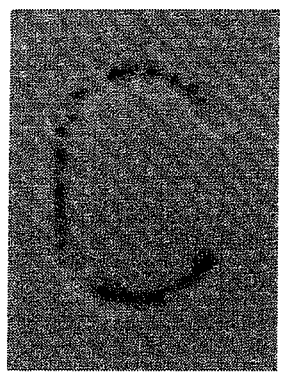 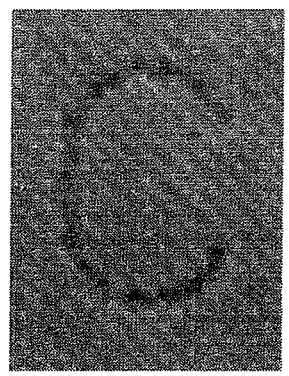 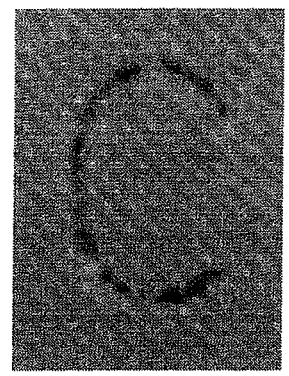
*FIG. 9D*  *FIG. 9E*  *FIG. 9F*
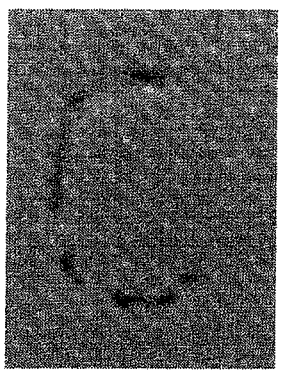 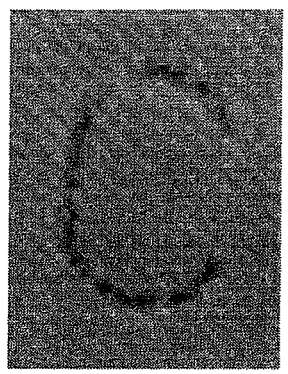 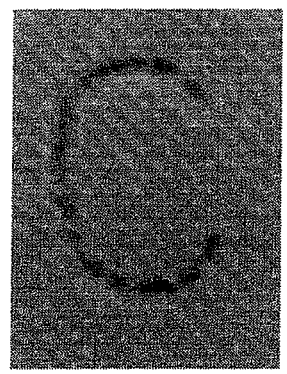
*FIG. 9G*  *FIG. 9H*  *FIG. 9I*
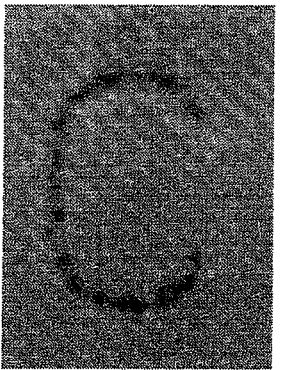 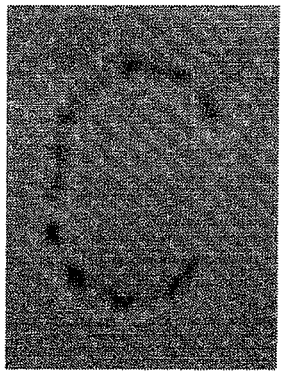 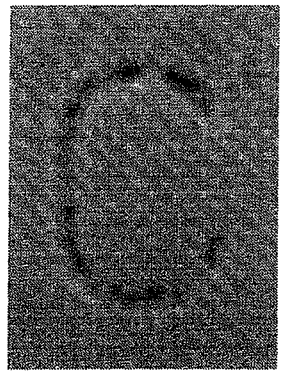
*FIG. 10*
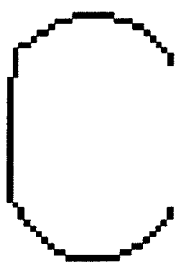

IMAGE PROCESSING SYSTEM, IMAGE PROCESSING APPARATUS AND COMPUTER READABLE MEDIUM

CROSS-REFERENCE TO RELATED APPLICATIONS

This application is based upon and claims priority under 35 USC 119 from Japanese Patent Application No. 2010-257515, filed Nov. 18, 2010.

BACKGROUND

Technical Field

The present invention relates to an image processing system, an image processing apparatus and a computer readable medium.

SUMMARY OF THE INVENTION

According to an aspect of the invention, an image processing system includes a first image processing apparatus and a second image processing apparatus. The first image processing apparatus includes a first image obtaining module, a first image extraction module, a first density extraction module, a first feature conversion module, a register module. The first image obtaining module obtains an image of an object having a seal impressed on a face thereof and having a film formed or laminated on the face thereof. The first image extraction module extracts a partial image of the seal within the image obtained by the first image obtaining module. The first density extraction module extracts a density of the partial image of the seal extracted by the first image extraction module. The first feature conversion module converts a density sequence formed by a sequence of the densities extracted by the first density extraction module into a feature of the partial image of the seal. The register module registers the features converted by the first feature conversion module and the densities extracted by the first density extraction module into storage module so that the features and the densities are associated with each other. The second image processing apparatus includes a second image obtaining module, a second image extraction module, a second density extraction module, a second feature conversion module, and a collation module. The second image obtaining module obtains an image of an object having a seal impressed on a face thereof and having a film formed or laminated on the face thereof. The second image extraction module extracts a partial image of the seal within the image obtained by the second image obtaining module. The second density extraction module extracts a density of the partial image of the seal extracted by the second image extraction module. The second feature conversion module converts a density sequence formed by a sequence of the densities extracted by the second density extraction module into a feature of the partial image of the seal. The collation module extracts a density corresponding to the feature converted by the second feature conversion module from the storage module and performs collation between the extracted density and the density extracted by the second density extraction module.

BRIEF DESCRIPTION OF THE DRAWINGS

Exemplary embodiments of the invention will be described in detail based on the following figures, wherein:

FIGS. 9A to 9I are explanatory diagrams showing examples of the partial image of a seal;

FIG. 10 is an explanatory diagram showing an example of a standard image for specifying the partial image of the seal;

DETAILED DESCRIPTION

Hereinafter, explanation will be made as to preferable exemplary embodiments for realizing the invention based on drawings.

Figure 1:
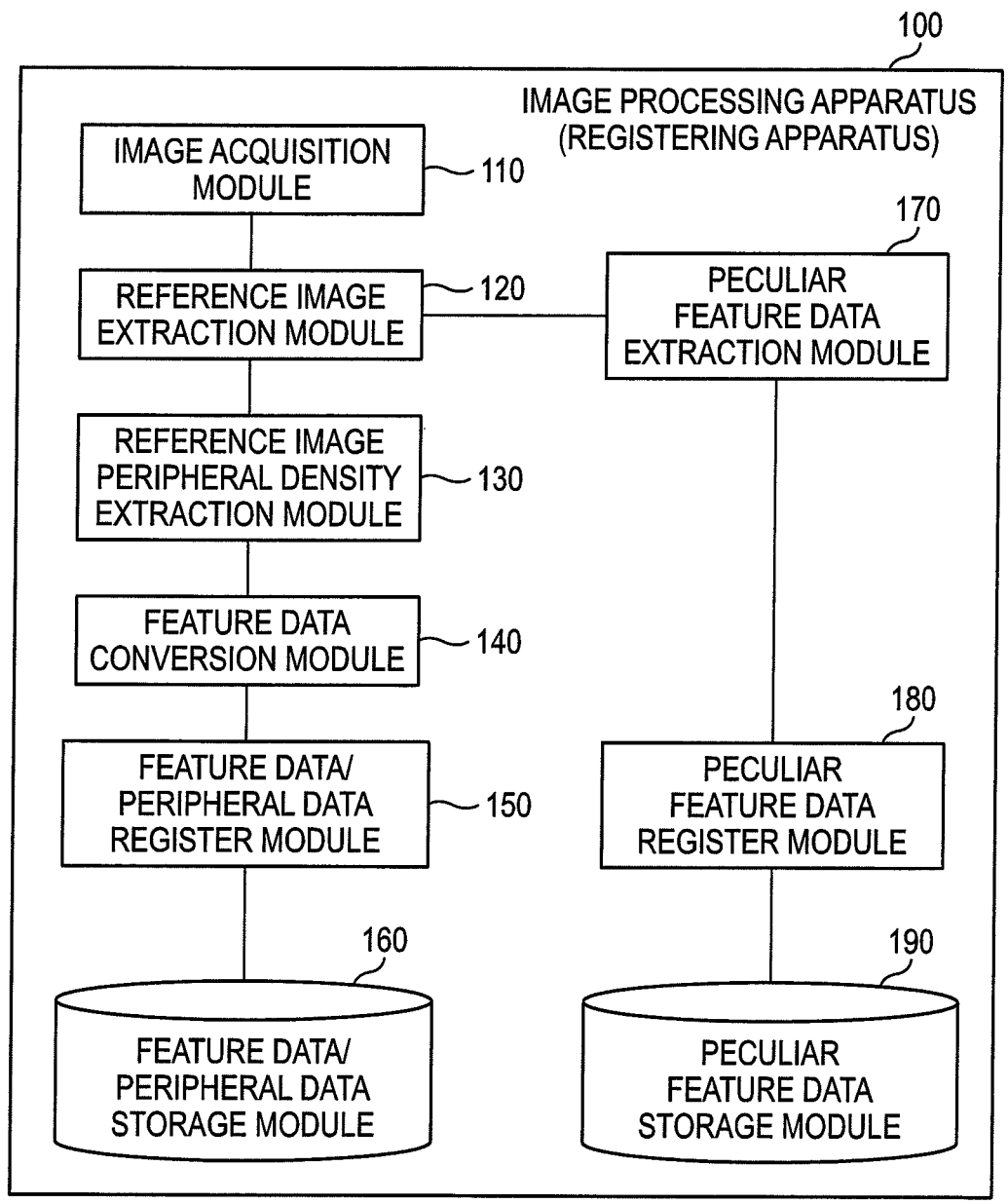
FIG. 1 is a schematic diagram showing the configuration of modules as to an example of the configuration of the exemplary embodiment (registering apparatus)

FIG. 1 is a schematic diagram showing the configuration of modules as to an example of the configuration of an image processing apparatus (registering apparatus) according to the exemplary embodiment.

The modules generally represents components such as softwares (computer programs) or hardwares capable of being separated logically. Thus, the modules in this embodiment represent not only modules of the computer programs but also modules of the hardware configuration. Thus, the exemplary embodiment also explains as to the computer programs for acting as these modules (programs for executing respective procedures by a computer, programs for acting the computer as respective means and programs for realizing respective functions by the computer), the system and the method. For convenience of explanation, although expressions "storing", "making store" and similar expressions are used, these expressions means "storing into a storage device" or "controlling so as to store in the storage device". Although the modules may be set so as to be one-to-one correspondence to the functions, at the time of mounting the modules, the single module may be configured by the single program, the plural modules may be configured by the single program, or the single module may be configured by the plural programs. Further, the plural modules may be executed by the single computer. The single module may be executed by the plural computers in a distributed processing or parallel processing environment. Another module may be contained in the single module. Hereinafter, "connection" is used in the case of a logical connection (transmission/reception of data, instruction, reference relation between data, etc.) as well as the physical connection. "Predetermined" means that a condition is determined before a target processing. That is, this expression means not only a case that a condition is determined before the processing of the exemplary embodiment but also means a case that a condition is determined according to a circumstance or a state at that time or a circumstance or a state up to that time before the target processing even after the processing according to the exemplary embodiment started.

Further, the system or the apparatus represents a case that it is realized by a single computer, hardware or apparatus etc. as well as a case that it is configured by connecting computers, hardwares and apparatuses etc. mutually via a communication means such as a network (including a communication coupling of one-to-one correspondence). Each of "the system" and "the apparatus" is used as a term of the same meaning. Of course, "the system" does not include a social "arrangement" (social system) which is a mere artificial arrangement.

Further, target information is read from the storage device upon the processing by each of the modules or upon each processing in the case of performing plural processings within the module, and the processing result is stored in the storage device after completing the processing. Thus, the explanation may be omitted as to the reading from the storage device before the processing and as to the storing into the storage device after the processing. The storage device may be a hard disk drive, a RAM (Random Access Memory), an external storage medium, a storage device coupled via a communication line, a register within a CPU (Central Processing Unit) etc.

The image processing apparatus (registering apparatus) according to the exemplary embodiment registers an image of an object as a reference for collating an object. As shown in an example of FIG. 1, an image processing apparatus (registering apparatus) 10 includes an image acquisition module 110, a reference image extraction module 120, a reference image peripheral density extraction module 130, a feature data conversion module 140, a feature data/peripheral data register module 150, a feature data/peripheral data storage module 160, a peculiar feature data extraction module 170, a peculiar feature data register module 180 and a peculiar feature data storage module 190. In the case where the authenticity can be determined based on the information stored in the feature data/peripheral data storage module 160, the image processing apparatus may be configured not to include any of the peculiar feature data extraction module 170, the peculiar feature data register module 180 and the peculiar feature data storage module 190.

The image acquisition module 110 is coupled to the reference image extraction module 120. The image acquisition module 110 obtains an image of an object having a seal impressed on the face thereof and also having a film formed or laminated thereon. The "object" is a solid object having a seal impressed on the face thereof and also having a film formed or laminated on the face after the impressing of the seal. As a concrete example, the object corresponds to a tablet of medicine. In the case of a tablet, "an image of the object" obtained by the image acquisition module 110 is an image obtained by imaging a tablet having been manufactured but before the procedure such as a wrapping or a bottling. The explanation as to the sealing and coating will be made later with reference to FIGS. 4 and 5. The imaging of an image will be explained by using FIG. 8. The obtaining of an image includes the reading of an image using a scanner or a camera etc. and the reading of an image stored in a hard disk (contained in the image processing apparatus and coupled via a network, for example), for example.

The reference image extraction module 120 is coupled to the image acquisition module 110, the reference image peripheral density extraction module 130 and the peculiar feature data extraction module 170. The reference image extraction module 120 extracts a partial image of the seal within the image obtained by the image acquisition module 110. In order to extract the partial image of the seal within the image, for example, an image at a predetermined position within the image may be extracted, an image at a predetermined position of the target object may be extracted, or an image having a predetermined feature may be extracted. The predetermined feature may be a portion where the entire length of a continuous line within the seal has a predetermined value or more and a portion configured by a curved line thereof has a predetermined length or more. Alternatively, in the case of an image at a position where distortion is likely generated as described later, that is, for example, in the case where the target object is a three-dimensional object, a partial image of the seal located at the curved face of the target object may be extracted. For example, when the target object entirely has a curved face like a tablet, the partial image of a seal at a portion other than the center portion of the target object may be extracted. The determination whether or not the target object is a three-dimensional object may be performed by using a sensor for detecting a three-dimensional shape, for example. When it is proved that the target object has a three-dimensional shape in advance, a value representing a three-dimensional object is set to a parameter representing whether or not the target object is a three-dimensional object, whereby the determination may be made in accordance with the parameter.

The partial image of the seal may be extracted in accordance with the pattern matching with an image having the aforesaid features. Alternatively, after extracting these features, the partial image of the seal may be extracted in accordance with the coincident rate in a feature space. For example, in order to extract these features, the length of a line within the seal is extracted to determine whether or not the extracted line is a curved line, and the length of the portion configured by the curved line is extracted. Then, it is determined whether or not these features satisfy the predetermined condition (for example, a predetermined value or more). The partial image of the seal will be explained later with reference to FIG. 9. Hereinafter, the partial image of the seal to be extracted will also be called as a reference image. The reference image provides a reference position for extracting peculiar feature data by the peculiar feature data extraction module 170. The partial image represents a part of the image with respect to the entire image of the object, and hence may be an image including the entirety of the seal or, of course, may be an image of the part of the seal.

The reference image peripheral density extraction module 130 is coupled to the reference image extraction module 120 and the feature data conversion module 140. The reference image peripheral density extraction module 130 extracts the density of the partial image of the seal extracted by the reference image extraction module 120. The "density of the partial image of the seal" may be the density of only the partial image of the seal, the density of the image of the seal portion and the peripheral portion thereof, or the density calculated by using these densities in accordance with a predetermined calculation method. The density of the partial image of the seal will be explained later with reference to FIGS. 12 to 15.

The feature data conversion module 140 is coupled to the reference image peripheral density extraction module 130 and the feature data/peripheral data register module 150. The feature data conversion module 140 converts a sequence of the densities extracted by the reference image peripheral density extraction module 130 into the feature of the partial image of the seal. This feature may be any kind of feature so long as it represents the feature of the partial image of the seal. The concrete example of the feature will be explained later with reference to FIG. 16.

The feature data/peripheral data register module 150 is coupled to the feature data conversion module 140 and the feature data/peripheral data storage module 160. The feature data/peripheral data register module 150 registers the feature thus converted by the feature data conversion module 140 and the density extracted by the reference image peripheral density extraction module 130 in a corresponding manner in the feature data/peripheral data storage module 160. That is, the registration is performed so that the feature is retrieved from the feature data/peripheral data storage module 160 and the density corresponding to the feature can be extracted. A single density (single density sequence) may correspond to the single feature or a plurality of densities (plural density sequences) may correspond to the single feature.

The feature data/peripheral data storage module 160 is coupled to the feature data/peripheral data register module 150. The feature data/peripheral data storage module 160 stores the feature converted by the feature data conversion module 140 and the density extracted by the reference image peripheral density extraction module 130 in the corresponding manner.

The peculiar feature data extraction module 170 is coupled to the reference image extraction module 120 and the peculiar feature data register module 180. The peculiar feature data extraction module 170 extracts an image at the predetermined position from the position of the extracted partial image of the seal. The "predetermined position from the position of the extracted partial image of the seal" corresponds, for example, to a rectangle etc. located at the position with predetermined distances respectively in the X-coordinate direction and the Y-coordinate direction from the position of the left top (may be right top, right bottom, left bottom or center etc.) of the circumscribed rectangle of the partial image of the seal. The "predetermined position" may be within the partial image of the seal. Hereinafter, the image at this position is also called peculiar feature data.

The peculiar feature data register module 180 is coupled to the peculiar feature data extraction module 170 and the peculiar feature data storage module 190. The peculiar feature data register module 180 registers the image extracted by the peculiar feature data extraction module 170 in the peculiar feature data storage module 190. That is, the image may be registered so that the image within the object can be extracted from the peculiar feature data storage module 190. For example, the image stored in the peculiar feature data storage module 190 is associated with an object identifier (tablet number etc. when the object is a tablet) for identifying the object which image is obtained by the image acquisition module 110. When the image of an object is determined to coincide by the collation procedure of an image processing apparatus (collating apparatus) 200 shown in FIG. 2 exemplarily, the object is determined to be the object having the object identifier.

The peculiar feature data storage module 190 is coupled to the peculiar feature data register module 180. The peculiar feature data storage module 190 stores the image extracted by the peculiar feature data extraction module 170.

Figure 2:
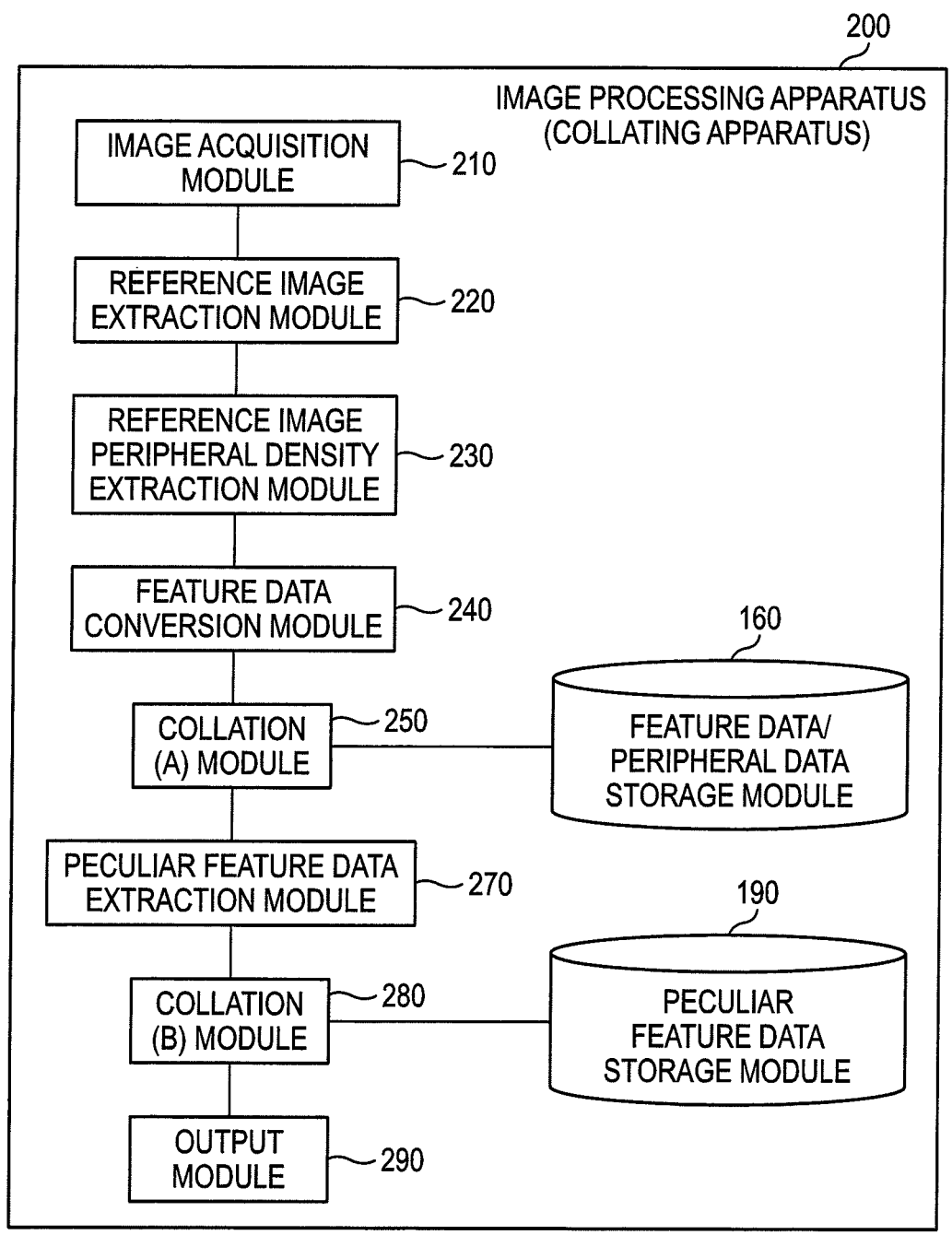
FIG. 2 is a schematic diagram showing the configuration of modules as to an example of the configuration of the exemplary embodiment (collating apparatus)

FIG. 2 is a schematic diagram showing the configuration of modules as to an example of the configuration of an image processing apparatus (collating apparatus) according to the exemplary embodiment. The image processing apparatus (collating apparatus) collates the images of the objects registered by the image processing apparatus (registering apparatus) 100 shown in FIG. 1 exemplarily with the image of the target object. As shown in an example of FIG. 2, the image processing apparatus (collating apparatus) 200 includes an image acquisition module 210, a reference image extraction module 220, a reference image peripheral density extraction module 230, a feature data conversion module 240, a collation (A) module 250, a feature data/peripheral data storage module 160, a peculiar feature data extraction module 270, a collation (B) module 280, a peculiar feature data storage module 190 and an output module 290. In the case where the authenticity can be determined based on the information stored in the feature data/peripheral data storage module 160, this image processing apparatus may be configured not to include any of the peculiar feature data extraction module 270, the collation (B) module 280 and the output module 290. In the figure, portions identical or similar to those of the image processing apparatus (registering apparatus) 100 shown in FIG. 1 exemplarily are referred to by the common symbols, with explanation thereof being omitted.

The image acquisition module 210 is coupled to the reference image extraction module 220. The image acquisition module 210 obtains an image of an object having a seal impressed on the face thereof and also having a film formed or laminated thereon. The object is equivalent to that explained in relation to the image acquisition module 110 of the image processing apparatus (registering apparatus) 100 shown in FIG. 1 exemplarily. However, this object is an object required for the collation. In the case of a tablet, the "object" of the "image of the object" obtained by the image acquisition module 210 is a tablet distributed in the market which is required for the collation in order to determine the authenticity etc.

The image acquisition module 210 may be arranged to obtain a plurality of images by changing the inclination of the object. To be concrete, the object may be imaged for plural times by changing the inclination of the object, the angle of an imaging apparatus and the illumination angle etc. This is to set the imaging condition of this image acquisition module so as to be same as that of the image acquisition module 110 of the image processing apparatus (registering apparatus) 100. That is, as to the object such as a tablet which easily inclines, since it is impossible to control the inclination of the object at the time of registration (in particular, at the time of registration in the case of the manufacturing process), the imaging of the object is generally performed only once. The imaging in the image acquisition module 210 of the image processing apparatus (collating apparatus) 200 is not necessarily same as the imaging at the time of registration. To be concrete, in the case where the object has a shape capable of inclining with respect to the center shafts of the optical system, the lenses, the image sensor of the imaging apparatus, the feature extracted from the obtained image may differ depending on the inclination with respect to the center shaft at the time of obtaining the image. Since the inclination with respect to the center shaft at the time of registration is unclear, the modules 210 of the image processing apparatus (collating apparatus) 200 obtains the images of the object for plural times with different inclination conditions with respect to the center shaft.

Further, in the case of imaging the object for plural times, the image acquisition module 210 may generate a single image from the imaged plural images. For example, a single image may be selected from the imaged plural images or a single image may be obtained by averaging the imaged plural images. Further, each of the reference image extraction module 220, the reference image peripheral density extraction module 230, the feature data conversion module 240 and the collation (A) module 250 may perform the processing of plural images obtained by the image acquisition module 210. To be concrete, for example, the reference image extraction module 220 extracts plural partial images from the plural images and the reference image peripheral density extraction module 230 extracts the densities of the plural partial images. As a result, there may arise a case that a sequence of the densities extracted by the reference image peripheral density extraction module 230 is converted into plural features by the feature data conversion module 240. Thus, there may also arise a case that plural densities (densities extracted from the feature data/peripheral data storage module 160) corresponding to the features are obtained. In this case, the collation (A) module 250 performs the collation between the plural densities extracted from the feature data/peripheral data storage module 160 and the plural densities extracted from the reference image peripheral density extraction module 230. When an object is determined to be same, one of the densities coincides therebetween. When two or more of the densities coincide, it may be determined that the collation is failure. The explanation will be made later with reference to FIGS. 4 and 5 as to the seal and the coating. Further, the explanation will be made later with reference to FIG. 8 as to the imaging of an image.

The reference image extraction module 220 is coupled to the image acquisition module 210 and the reference image peripheral density extraction module 230. The reference image extraction module 220 extracts the partial image of the seal within an obtained image. This method of extracting the partial image of the seal is equivalent to that explained above in relation to the reference image extraction module 120 of the image processing apparatus (registering apparatus) 100 shown in FIG. 1 exemplarily. The partial image of the seal will be explained later with reference to FIG. 9.

The reference image peripheral density extraction module 230 is coupled to the reference image extraction module 220 and the feature data conversion module 240. The reference image peripheral density extraction module 230 extracts the density of the partial image of the seal extracted from the reference image extraction module 220. This method of extracting the density of the partial image of the seal is equivalent to that explained above in relation to the reference image peripheral density extraction module 130 of the image processing apparatus (registering apparatus) 100 shown in FIG. 1 exemplarily. The density of the partial image of the seal will be explained later with reference to FIGS. 12 to 15.

The feature data conversion module 240 is coupled to the reference image peripheral density extraction module 230 and the collation (A) module 250. The feature data conversion module 240 converts a sequence of the densities extracted by the reference image peripheral density extraction module 230 into the feature of the partial image of the seal. This feature is equivalent to that explained above in relation to the feature data conversion module 140 of the image processing apparatus (registering apparatus) 100 shown in FIG. 1 exemplarily. The concrete example of the feature will be explained later with reference to FIG. 16.

The collation (A) module 250 is coupled to the feature data conversion module 240, the feature data/peripheral data storage module 160 and the peculiar feature data extraction module 270. The collation (A) module 250 extracts, from the feature data/peripheral data storage module 160, the density corresponding to the feature obtained by the conversion processing of the feature data conversion module 240 and collates the extracted density with the density extracted by the reference image peripheral density extraction module 230. This collation may be the collation for determining the authenticity etc. Alternatively, in the case where the collation (B) module 280 performs the collation for determining the authenticity etc., the collation (A) module extracts a collation candidate for the collation by the collation (B) module 280.

The feature data/peripheral data storage module 160 is coupled to the collation (A) module 250. The feature data/peripheral data register module 150 of the image processing apparatus (registering apparatus) 100 registers the feature of the partial image of the seal as a reference and the density of the partial image of the seal in a corresponding manner in the feature data/peripheral data storage module 160.

The peculiar feature data extraction module 270 is coupled to the collation (A) module 250 and the collation (B) module 280. The peculiar feature data extraction module 270 extracts an image located at a predetermined position from the position of the partial image of the seal extracted by the reference image extraction module 220. The predetermined position from the position of the partial image of the seal is equivalent to that explained in relation to the peculiar feature data extraction module 170 of the image processing apparatus (registering apparatus) 100 shown in FIG. 1 exemplarily.

The collation (B) module 280 is coupled to the peculiar feature data extraction module 270, the peculiar feature data storage module 190 and the output module 290. The collation (B) module 280 extracts an image from the peculiar feature data storage module 190 and collates the extracted image with the image extracted by the peculiar feature data extraction module 270. The collation processing of the collation (B) module 280 will be explained later.

The peculiar feature data storage module 190 is coupled to the collation (B) module 280. The peculiar feature data storage module 190 registers the images extracted by the peculiar feature data extraction module 170 of the image processing apparatus (registering apparatus) 100 shown in FIG. 1 exemplarily.

The output module 290 is coupled to the collation (B) module 280. The output module 290 outputs the collation result obtained by the collation (B) module 280 (or the collation (A) module 250). The collation result is the determination result of the authenticity (determination result as to whether or not manufactured by a target factory or a manufacturing apparatus etc.), for example. The outputting of the collation result is to print out by a printing apparatus such as a printer, to display on a display apparatus such as a display, to store in a storage medium such as a memory card or to send to other information processing apparatus, for example.

Figure 3:
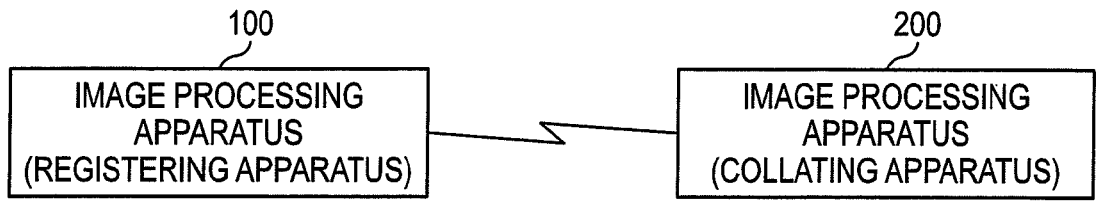
FIG. 3 is an explanatory diagram showing an example of the system configuration in the case of realizing the exemplary embodiment.

FIG. 3 is an explanatory diagram showing an example of the system configuration in a case of realizing the exemplary embodiment. The image processing apparatus (registering apparatus) 100 shown in FIG. 1 exemplarily and the image processing apparatus (collating apparatus) 200 shown in FIG. 2 exemplarily are coupled via a communication line. For example, the image processing apparatus (registering apparatus) 100 is installed in a factory etc. manufacturing tablets and registers the images of manufactured tablets. The image processing apparatus (collating apparatus) 200 performs the collation processing in order to determine whether or not each of tablets distributed in the market is manufactured by the factory etc. In this case, the respective information stored in the feature data/peripheral data storage module 160 and the peculiar feature data storage module 190 of the image processing apparatus (registering apparatus) 100 is transferred to the feature data/peripheral data storage module 160 and the peculiar feature data storage module 190 of the image processing apparatus (collating apparatus) 200, respectively. Alternatively, the image processing apparatus (registering apparatus) 100 may register the respective information into the feature data/peripheral data storage module 160 and the peculiar feature data storage module 190 of the image processing apparatus (collating apparatus) 200 via the communication line. On the contrary, the image processing apparatus (collating apparatus) 200 may perform the collation processing by using the feature data/peripheral data storage module 160 and peculiar feature data storage module 190 of the image processing apparatus (registering apparatus) 100 via the communication line. Alternatively, both the feature data/peripheral data storage module 160 and the peculiar feature data storage module 190 may be disposed in an image processing apparatus (server etc.) other than the image processing apparatus (registering apparatus) 100 and the image processing apparatus (collating apparatus) 200 and each of the image processing apparatus (registering apparatus) 100 and the image processing apparatus (collating apparatus) 200 may access these modules via the communication lines.

Explanation will be made as to the general manufacturing process of tablets.

(1) Mixture: Principal agent having an active component, diluting agent, binding agent, disintegrant etc. are mixed and uniformized.

(2) Granulation: Grains each having uniform shape and size are formed form the mixed material.

(3) Mixture: Additive such as lubricant pharmaceuticals is mixed.

Figure 4:
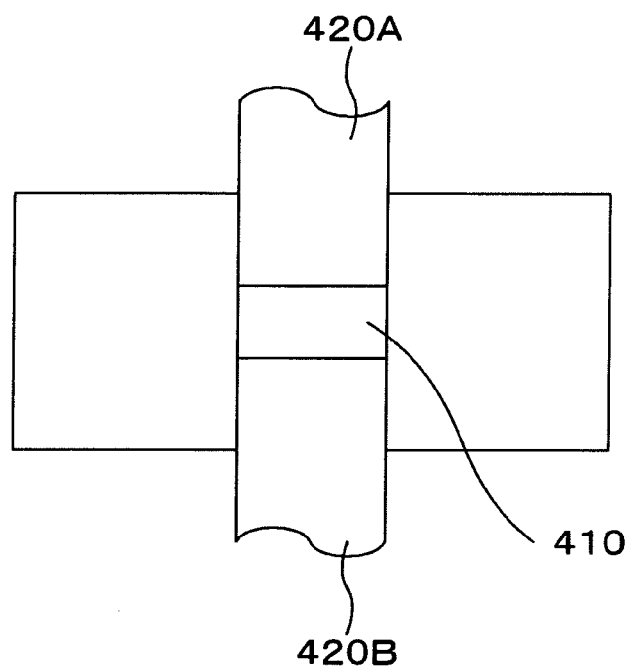
FIG. 4 is an explanatory diagram showing an example of the process of tablet making.

(4) Tablet making: Mechanical external force is applied to powder within a mortar between upper and lower stampers to thereby perform compression molding. FIG. 4 is an explanatory diagram showing an example of the process of the tablet making. A tablet 410 is applied with a force, compressed and marked with the name of the drag (may be a number etc.) by upper and lower stampers 420A and 420B. The name of the drag is formed on the face of one of the stampers 420A and 420B contacting with the tablet 410 by a convex or concave configuration. In general, the face of one of the stampers 420A and 420B contacting with the tablet 410 is formed by a curved face and hence the tablet is formed to have the curved face.

Figure 5:
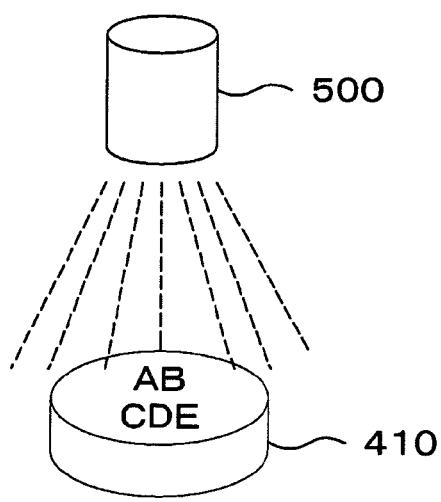
FIG. 5 is an explanatory diagram showing an example of the coating process of a tablet.

(5) Coating: A film is formed or laminated on the face of the tablet by high polymer or sucrose etc. or by mixing the high polymer or sucrose etc. with various kinds of powder etc. FIG. 5 is an explanatory diagram showing an example of the coating process of the tablet. A coating apparatus 500 sprays the high polymer or sucrose etc. in a misty liquid state toward the tablet 410 to thereby perform the coating. An irregular deformation (for example, the deformation due to a fact that the coating material is buried in the seal portion with thin and thick states) is generated since such the process (in particular, the coating process) is performed. The deformation can be observed along the seal the seal is stamped with the mold of the same size in the tablet making process.

(6) Inspection: An inspection is performed in order to remove defective tablets. In this case, the image processing apparatus (registering apparatus) 100 shown in FIG. 1 exemplarily images respective tablets and registers the images thereof.

(7) Encasement: In order to prevent the change of properties, degradation and pollution etc. of the tablets as drug medicines and to protect the tablets by predetermined encasement material, the tablets are encapsulated or encased.

Figure 6:
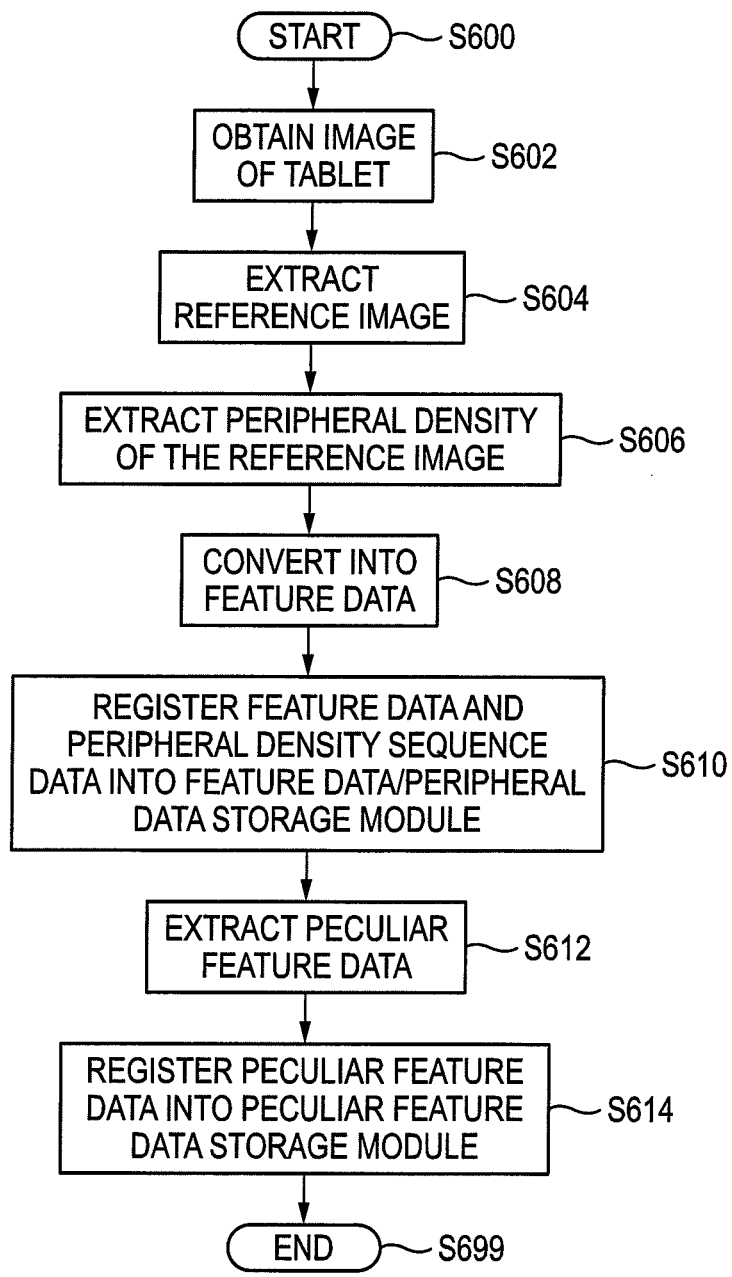
FIG. 6 is a flowchart showing an example of the processing according to the exemplary embodiment (registering apparatus)

FIG. 6 is a flowchart showing an example of the processing performed by the image processing apparatus (registering apparatus) 100 according to the exemplary embodiment.

Figure 8:
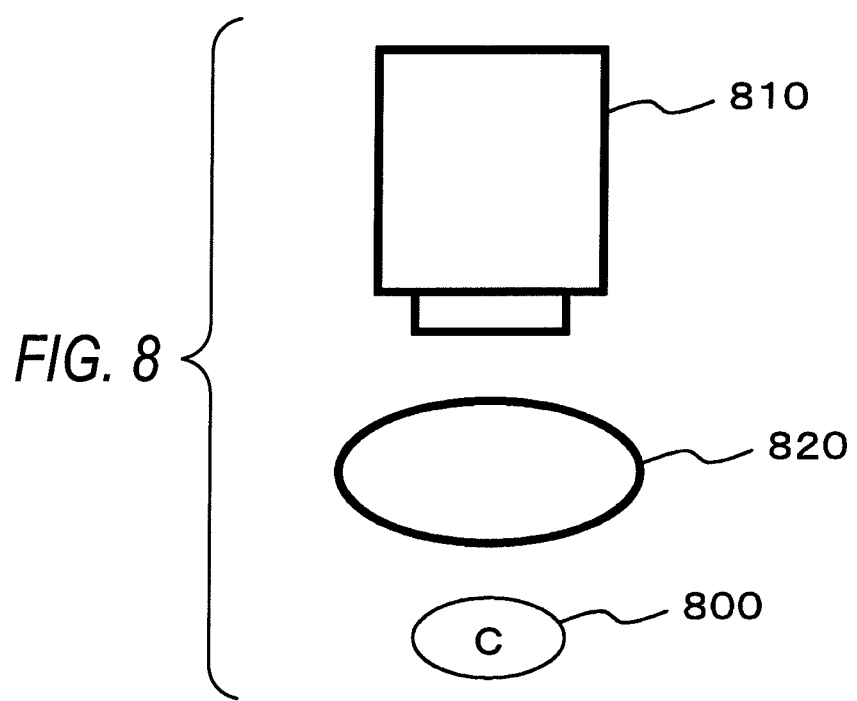
FIG. 8 is an explanatory diagram showing an example of the processing performed by an image acquisition module.

In step S602, the image acquisition module 110 obtains an image of the tablet having been sealed and coated. FIG. 8 is an explanatory diagram showing an example of the processing by the image acquisition module 110. For example, an imaging apparatus (digital camera) 810 images a tablet 800 illuminated by an illumination 820. The illumination 820 is desirably arranged to illuminate light uniformly toward the entire peripheral direction of the tablet so as not to form any shade portion.

Figure 11A:
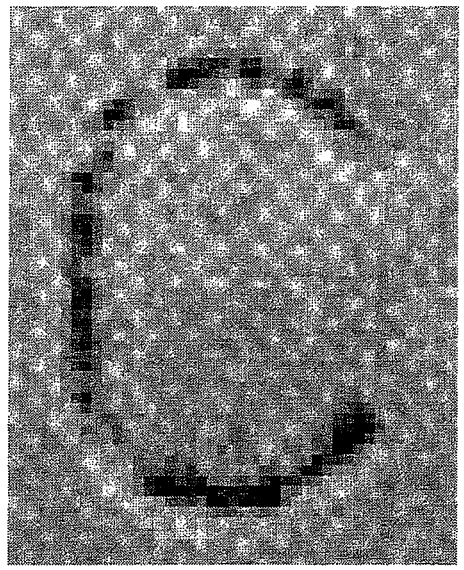
FIGS. 11A and 11B are explanatory diagrams showing examples of the rotation of the partial image of the seal.
Figure 11B:
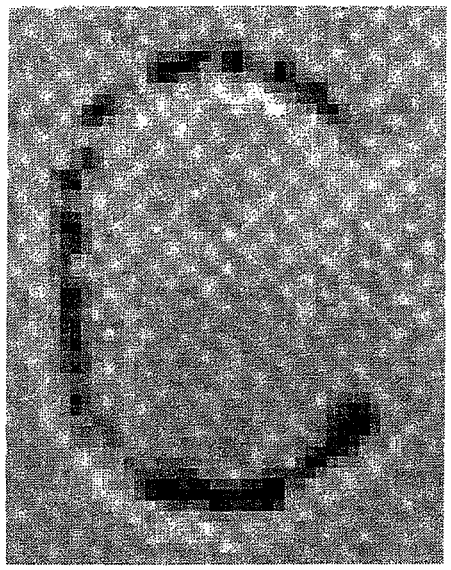

In step S604, the reference image extraction module 120 extracts the reference image. FIG. 9 is explanatory diagrams showing examples of the reference image as the partial image of the tablet. Each of these drawings shows a case where the character image of "C", for example, is extracted from the imaged image of the tablet as the reference image from the seal formed by characters and symbols. FIG. 9A to 9I show the cases where the reference images "C" are extracted from nine tablets, respectively. It is clear from these drawings that irregular deformation appears in the image of "C". This reference image "C" is extracted in a manner, for example, that the reference image "C" is specified and extracted according to the pattern patching using a standard image shown in FIG. 10 exemplarily. The reference image thus extracted may be subjected to the image processing. For example, the image shown in FIG. 11A is the extracted reference image, whilst the image shown in FIG. 11B is the reference image subjected to a rotating processing. The image processing may be, for example, a parallel moving processing, an affine transformation processing such as an expansion/contraction processing, a noise removing processing or a density conversion processing instead of the rotating processing.

The standard image is an image for extracting the reference image from the image of an object. For example, the standard image may be generated by imaging the seal of the stamper 420A or 420B or by averaging a plurality of reference images.

Figure 12A:
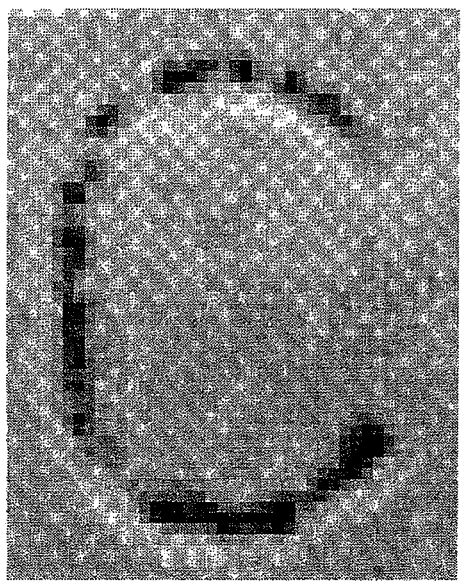
FIGS. 12A and 12B are explanatory diagrams showing extracted examples of the peripheral density of the partial image of the seal.
Figure 12B:
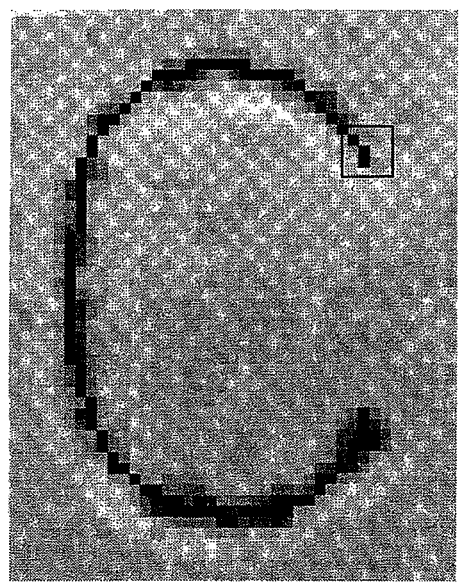
Figure 13:
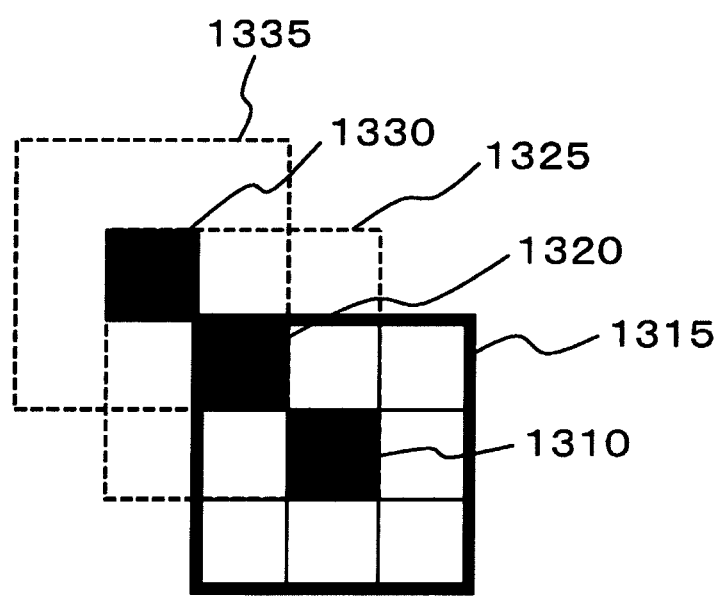
FIG. 13 is an explanatory diagram showing an example of the relation between standard pixels and reference pixels.

In step S606, the reference image peripheral density extraction module 130 extracts the peripheral density of the reference image. FIG. 12 is an explanatory diagram showing an example of the extraction of the peripheral density of the reference image which is the partial image of the seal. FIG. 12A shows an example of the reference image, whilst FIG. 12B shows an example of an image obtained by superimposing the standard image shown in FIG. 10 exemplarily on the reference image. The density of the reference image is extracted based on pixels thereof at positions of the respective black pixels of the standard image. For example, as shown in the example of FIG. 13, a sequence of statistical values (average value, mode value, center value etc., for example) of the densities of peripheral nine pixels around the position of each of the black pixels (83 pixels such as standard pixels 1310, 1320, 1330 in this case) of the standard image is set as the density of the reference image. In the example of FIG. 13, the peripheral nine pixels are peripheral pixels 1315 including the pixel of the reference image located at the position of the standard pixel 1310, peripheral pixels 1325 including the pixel of the reference image located at the position of the standard pixel 1320, peripheral pixels 1335 including the pixel of the reference image located at the position of the standard pixel 1330, etc. Of course, the density of the reference image may be the density obtained based on peripheral twenty-five pixels etc. in place of the peripheral nine pixels, or the density of the pixel of the reference image located at the position of the standard pixel, or the density of pixels within a circular range in place of the rectangular range. Although the density is extracted in a manner that the standard image is superimposed on the reference image and the densities of the pixels at the superimposed positions are used. However, the exemplary embodiment is not limited thereto and it is sufficient to extract the density based on the densities within the reference image. For example, the density may be extracted based on the densities of all pixels within the reference image or based on the densities of pixels within the reference image each having a predetermined density or more.

Figure 14:
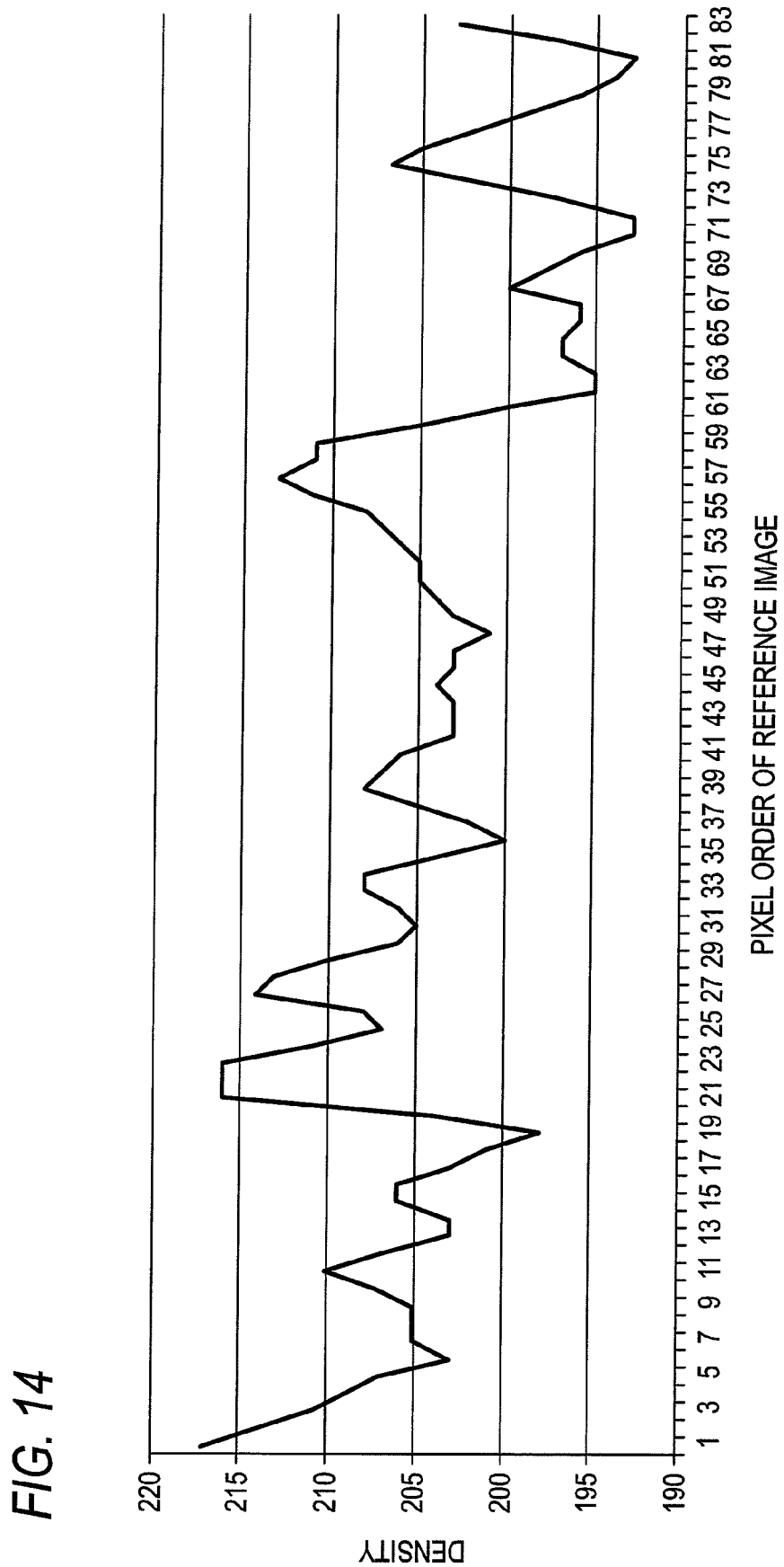
FIG. 14 is an explanatory diagram showing an example of peripheral density sequence data.
Figure 15A:
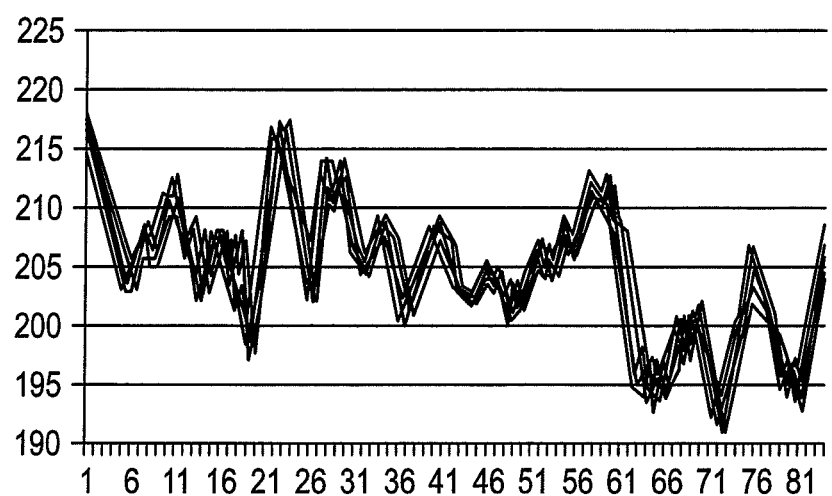
FIGS. 15A to 15I are explanatory diagrams showing other examples of peripheral density sequence data.
Figure 15B:
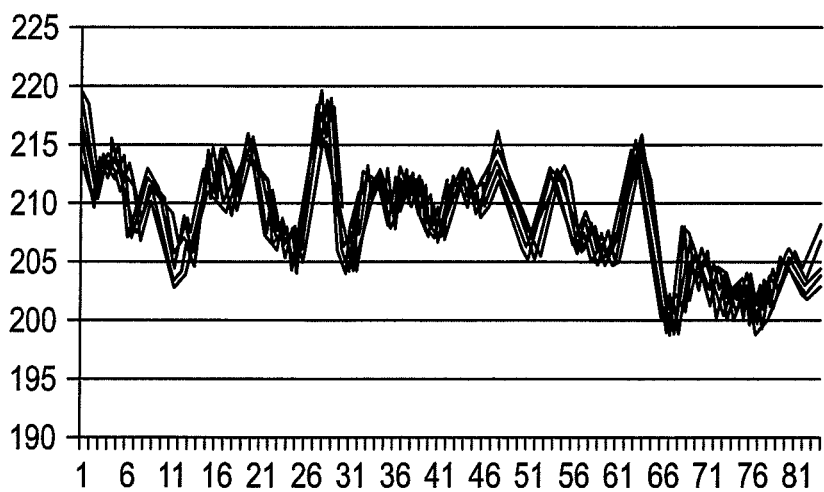
Figure 15C:
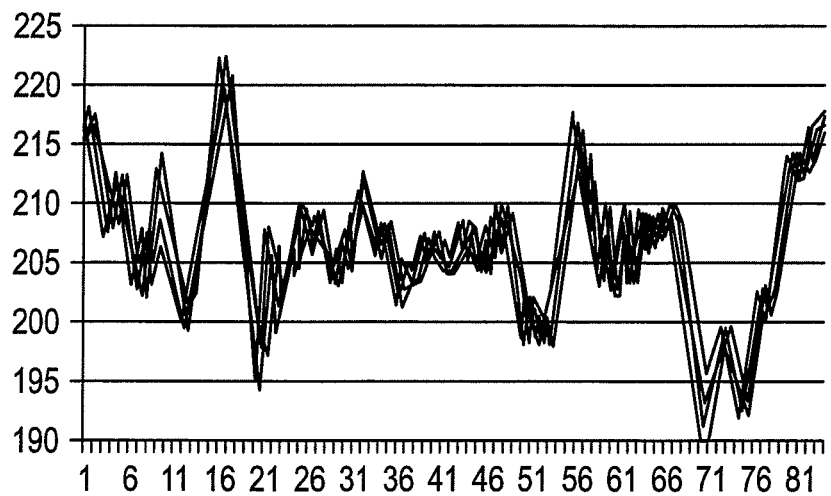
Figure 15D:
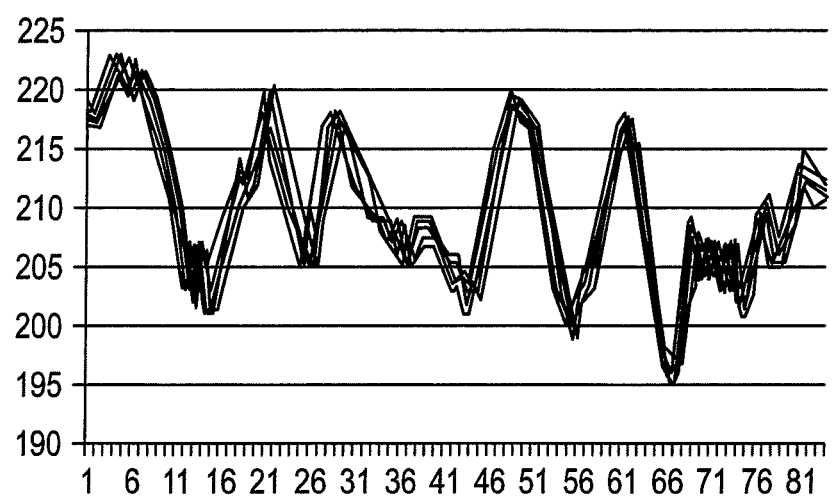
Figure 15E:
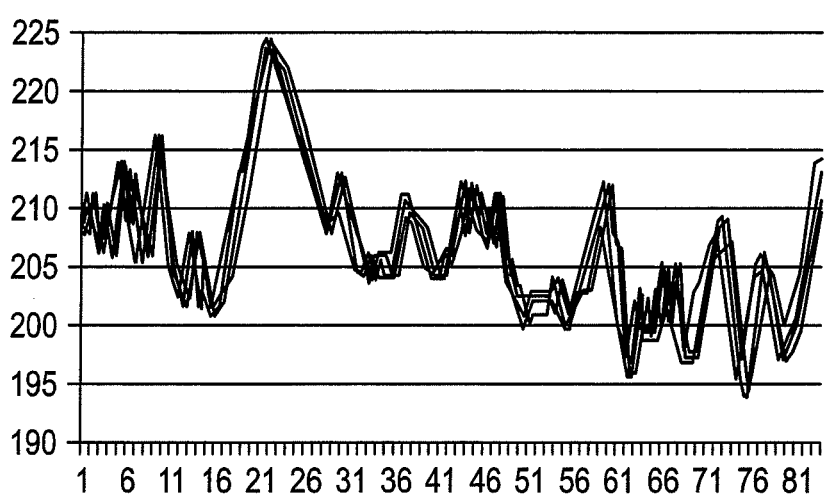
Figure 15F:
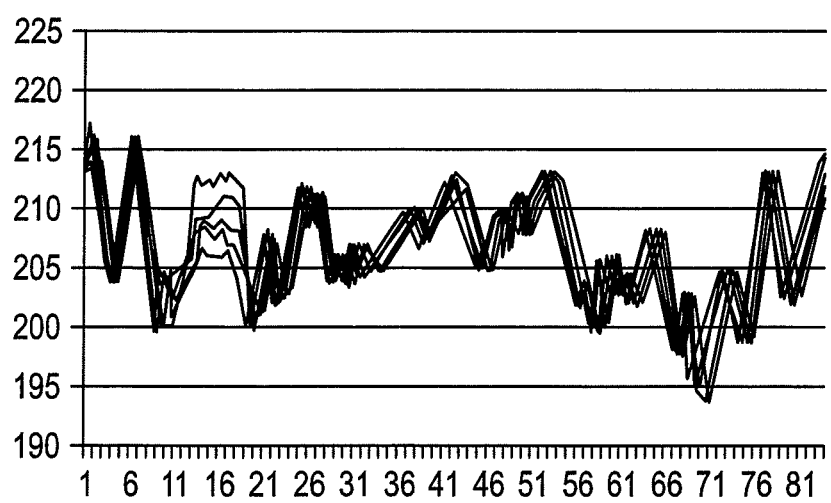
Figure 15G:
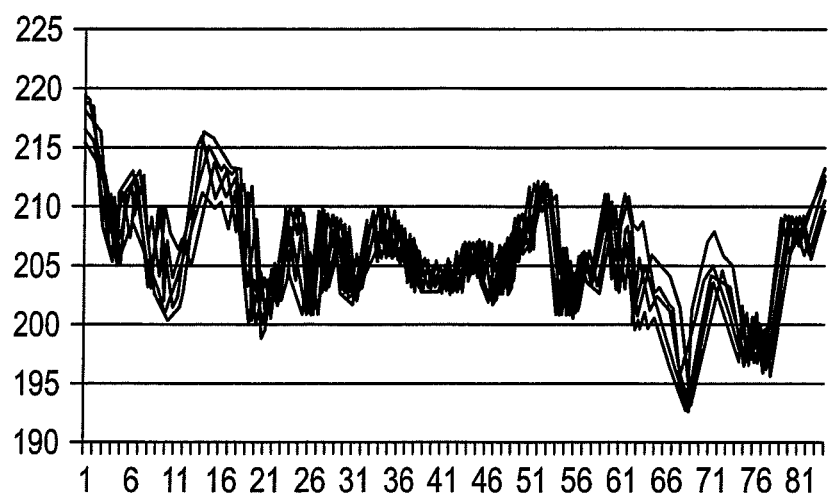
Figure 15H:
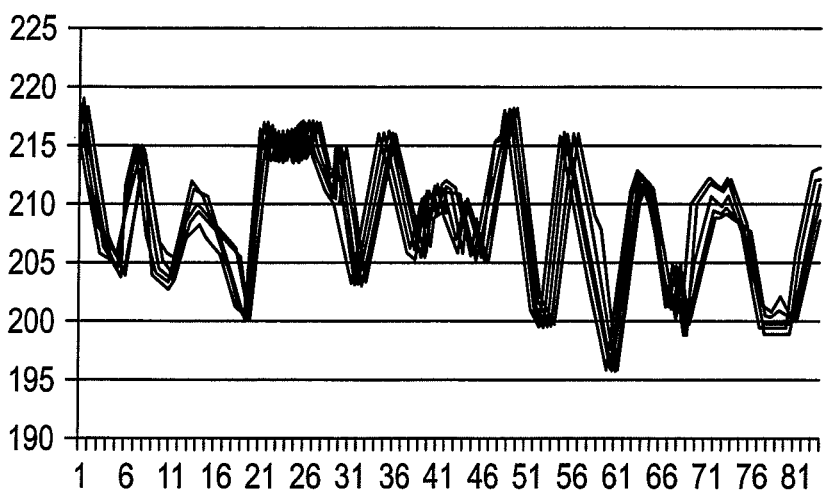
Figure 15I:
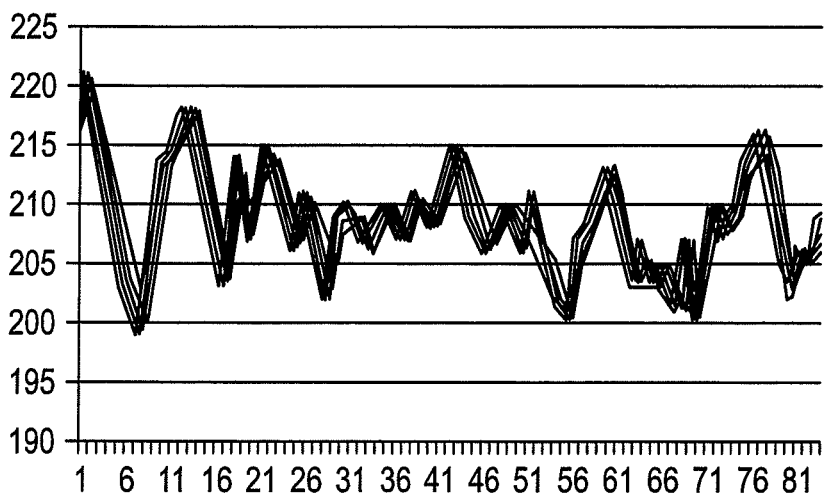

FIG. 14 is an explanatory diagram showing an example of peripheral density sequence data. This figure is a graph (ordinate: density, abscissa: pixel order of reference image) showing the peripheral density sequence of the reference image shown in FIG. 12B exemplarily and this figure shows the densities of 83 pixels. The pixel order of reference image is a predetermined order. For example, the pixel order may be determined in a manner that, for example, the rectangle (upper end pixel of "C") shown in FIG. 12B exemplarily is determined as the first pixel and the numbers are determined sequentially along the drawing order to the 83-th pixel.

FIG. 15 is explanatory diagrams showing an example of peripheral density sequence data of the reference images shown in FIGS. 9A to 9I exemplarily. As clear from the graphs of this figure, although each of the reference images represents the same character "C", these graphs of the respective reference images represent different configurations since the image of the character is deformed. Each of the graphs is formed by plural lines since the object is imaged plural times (ten times in this example) under different conditions and obtained densities are plotted in the graph. This means that the difference of the shape of the graph is not so large among the respective imaging operations.

Figure 16:
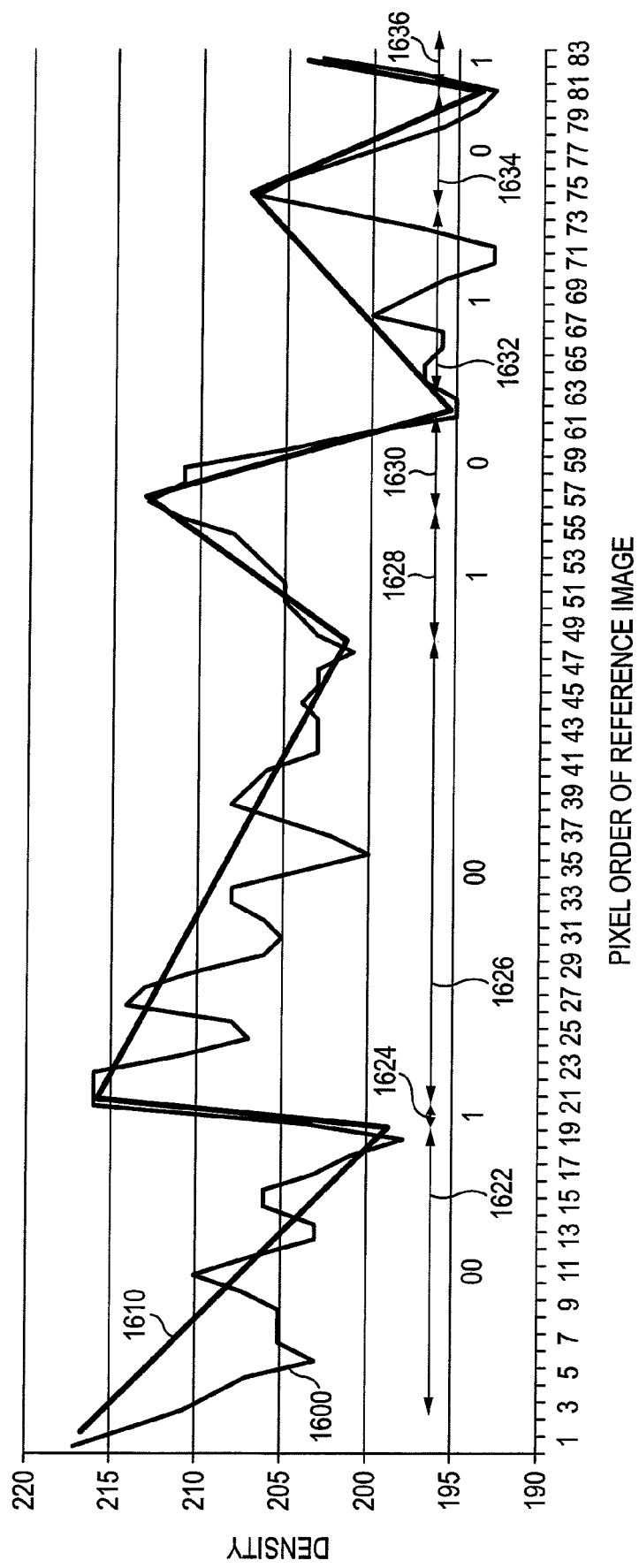
FIG. 16 is an explanatory diagram showing an example of the peripheral density sequence data and feature data.

In step S608, the feature data conversion module 140 converts the peripheral density sequence data into the feature data. FIG. 16 is an explanatory diagram showing an example of a peripheral density data sequence 1600, a converted data sequence 1610 and feature data. The feature data shown in FIG. 16 is obtained in a manner that the peripheral density data sequence 1600 is converted into the converted data sequence 1610 formed by frequency components (large frequency components) of predetermined value or more of the peripheral density data sequence and the converted data sequence 1610 is subjected to a digitizing processing. The digitizing processing is performed in a manner that the reduction and the increase are respectively represented by "0" and "1", and "0" or "1" is repeated for plural times (two times n this case) when the length of the reduction or the increase is a predetermined value or more. Thus, a section 1622 is "00", a section 1624 is "1", a section 1626 is "00", a section 1628 is "1", a section 1630 is "0", a section 1632 is "1", a section 1634 is "0" and a section 1636 is "1". According to this conversion method, the peripheral density data sequence 1600 shown in FIG. 16 exemplarily is converted into the feature data "0010010101". According to this conversion method, there may arise a case that different pieces of peripheral density sequence data are converted into the same feature data. This means that the peripheral density sequence data is classified by the feature data. A method other than this conversion method may be employed so long as the peripheral density sequence data can be converted into the feature data.

In step S610, the feature data/peripheral data register module 150 registers the feature data and the peripheral density sequence data into the feature data/peripheral data storage module 160. In the example shown in FIG. 16, the feature data "0010010101" and is the peripheral density data sequence 1600 are registered in the feature data/peripheral data storage module 160 in a corresponding manner.

In step S612, the peculiar feature data extraction module 170 extracts the peripheral feature data. That is, an image at the predetermined position is extracted from the image of the tablet with reference to the position of the reference image.

In step S614, the peculiar feature data register module 180 registers the peripheral feature data into the peculiar feature data storage module 190.

In the case where the image processing apparatus is configured not to include any of the peculiar feature data extraction module 170, the peculiar feature data register module 180 and the peculiar feature data storage module 190, each processing of step S612 and step S614 is not performed.

Figure 7:
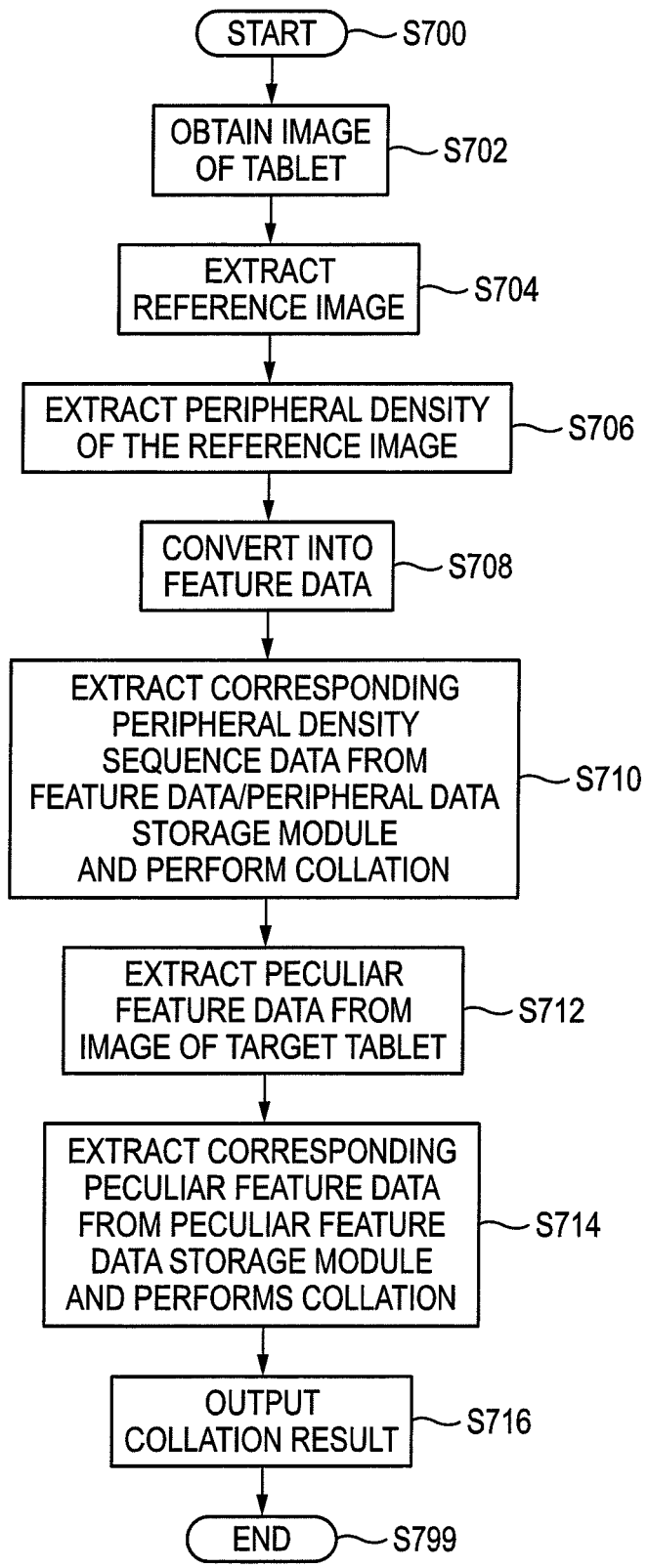
FIG. 7 is a flowchart showing an example of the processing according to the exemplary embodiment (collating apparatus)

FIG. 7 is a flowchart showing an example of the processing performed by the image processing apparatus (collating apparatus) 200 according to the exemplary embodiment.

In step S702, the image acquisition module 210 obtains an image of the tablet. This step performs the processing equivalent to that of step S602 shown in FIG. 6 exemplarily. The image of a target tablet is the image of a table as a reference (image of the tablet having been manufactured in a factory etc.) in the example of FIG. 6, whilst the image of a target tablet is the image of a tablet as a subject for collation in the example of FIG. 7.

In step S704, the reference image extraction module 220 extracts the reference image. This step performs the processing equivalent to that of step S604 shown in FIG. 6 exemplarily.

In step S706, the reference image peripheral density extraction module 230 extracts the peripheral density of the reference image. This step performs the processing equivalent to that of step S606 shown in FIG. 6 exemplarily.

In step S708, the feature data conversion module 240 converts the extracted peripheral density into the feature data. This step performs the processing equivalent to that of step S608 shown in FIG. 6 exemplarily.

Figure 17:
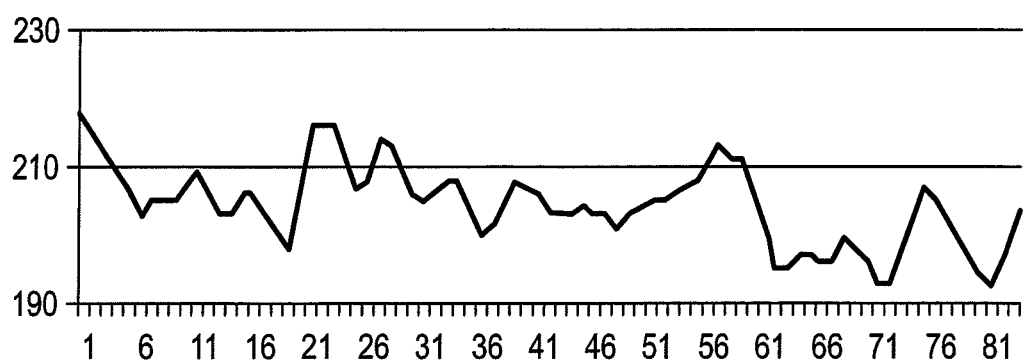
FIG. 17 is an explanatory diagram showing an example of the registered peripheral density sequence data.
Figure 18:
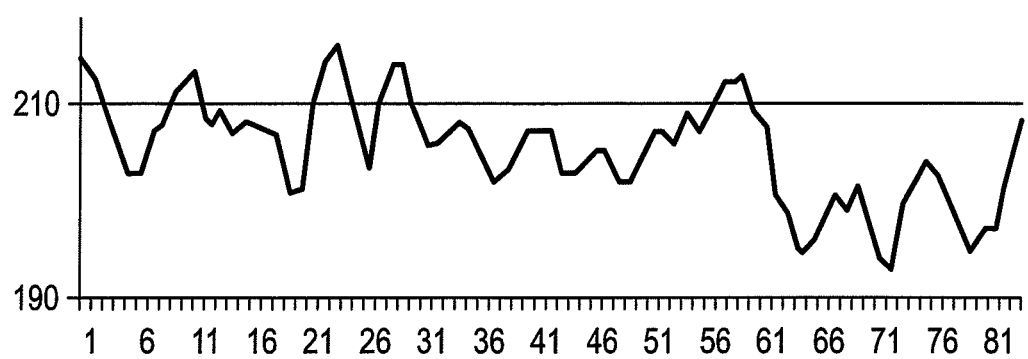
FIG. 18 is an explanatory diagram showing an example of the peripheral density sequence data to be collated.

In step S710, the collation (A) module 250 extracts corresponding peripheral density sequence data from the feature data/peripheral data storage module 160 and performs the collation. That is, the collation (A) module extracts the peripheral density sequence data corresponding to the feature data from the feature data/peripheral data storage module 160 and collates with the peripheral density sequence data extracted in step S706. For example, the collation is performed by using the normalized correlation method. To be concrete, in the case where the feature data "0010010101" is obtained in step S708, the peripheral density sequence data (see the graph exemplarity shown in FIG. 17) corresponding thereto is fetched from the feature data/peripheral data storage module 160 and is collated with the peripheral density sequence data (see the graph exemplarity shown in FIG. 18) extracted in step S706. When the respective data does not coincide to each other as the result of the collation process (when it is determined to be a fake), the process proceeds to step S716 without performing steps S712 and S714.

In step S712, the module 712 extracts the peculiar feature data from the image of a target tablet. This step performs the processing equivalent to that of step S612 shown in FIG. 6 exemplarily.

In step S714, the collation (B) module 280 extracts corresponding peculiar feature data from the peculiar feature data storage module 190 and performs the collation. For example, an authenticity determining method explained later is employed.

In step S716, the output module 290 outputs the collation result.

In the case where the image processing apparatus is configured not to include any of the peculiar feature data extraction module 270, the collation (B) module 280 and the peculiar feature data storage module 190, each processing of step S712 and step S714 is not performed.

The collation method in the collation (B) module 280 may be the following authenticity determining method.

<A1>

An authenticity determination method for determining the authenticity of objects which readable peculiar feature having randomness is distributed along the face thereof, the method is characterized by including the steps of:

obtaining reference data representing a feature distributed on a true object obtained by reading the feature of the true object in advance;

obtaining collation data representing the feature distributed on an object to be determined by reading the feature of the object to be determined;

repeatedly calculating correlation values between data representing the feature distributed in a first area of a predetermined size on one of the true object and the object to be determined and data representing the feature distributed in a second area having the same size as the first size on the other object while moving the position of the second area on the other object within an area larger than the predetermined size; and determining the authenticity of the object to be determined based on whether or not the maximum value of the correlation values obtained by the calculation is equal to or larger than a first predetermined value and whether or not the normalized score of the maximum value of the correlation values that is obtained by dividing a value, resulted by reducing the average value of the correlation values from the maximum value of the correlation values, by the standard deviation of the correlation values is equal to or larger than a second predetermined value.

<A2>

The authenticity determination method described in <A1>, wherein the feature of the object can be read optically, and the reference data and the collation data is image data obtained by irradiating light on the true object and the object to be determined and by reading reflection light or transmission light.

<A3>

The authenticity determination method described in <A2>, wherein the object is a tablet and the feature of the object is read by a flatbed scanner.

<A4>

The authenticity determination method described in <A1>, wherein the correlation values are calculated by a normalized correlation method.

<A5>

The authenticity determination method described in <A2>, wherein a tone value range, which is estimated to contain a noise component, is set based on the distribution of the tone values with respect to at least one of the reference data and the collation data, and the correlation values are calculated after removing the data belonging to the tone value range thus set.

<A6>

The authenticity determination method described in <A5>, wherein the reference data is obtained by reading, from a predetermined medium, reference data which is obtained by optically reading the feature of the true object and recorded in the predetermined medium, then the tone value range, which is estimated to contain a noise component with respect to the reference data, is set based on the distribution of the tone values of the reference data thus obtained, and the correlation values are calculated after removing the data belonging to the tone value range thus set from the reference data.

<A7>

The authenticity determination method described in <A5> or <A6>, wherein as the range estimated to contain the noise component, there is set a range from the maximum or minimum value of the tone value to a value where an accumulation frequency reaches a predetermined value or a range where the tone value is $AVE+n\sigma$ or more or the tone value is $AVE-n\sigma$ or less supposing that the average value of the tone values is AVE, the standard deviation of the distribution of the tone values is $\sigma$ and predetermined value is n.

Figure 19:
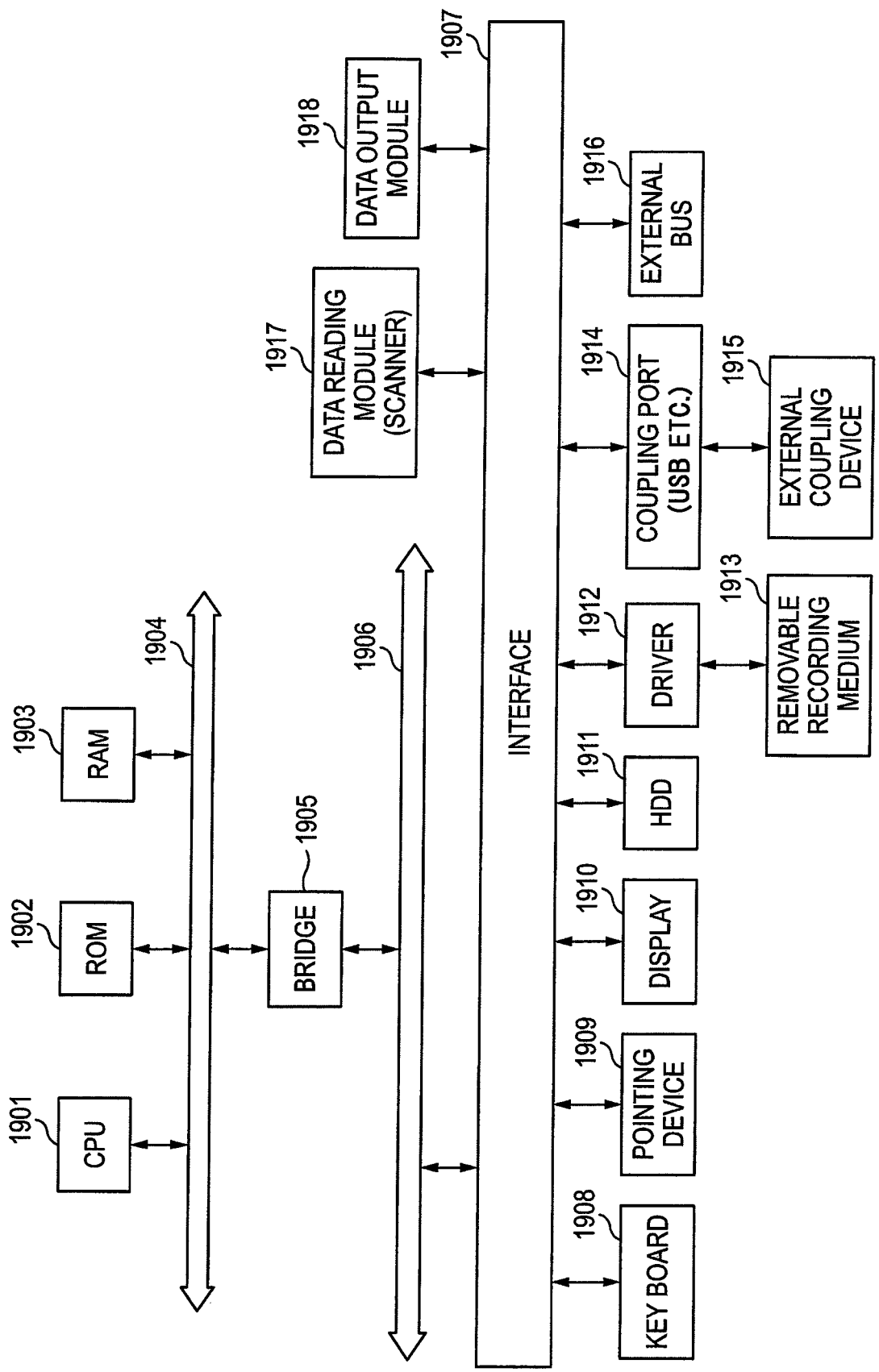
FIG. 19 is a block diagram showing an example of the hardware configuration of a computer for realizing the exemplary embodiment.

An example of the hardware configuration of the image processing apparatus (registering apparatus) and the image processing apparatus (collating apparatus) according to the exemplary embodiment will be explained with reference to FIG. 19. The configuration shown in FIG. 19 is configured by a personal computer (PC) etc., for example, and shows an example of the hardware configuration including a data reading portion 1917 such as a scanner and a data output portion 1918 such as a printer.

A CPU (Central Processing Unit) 1901 is a control portion which executes the processing according to the computer program describing the execution sequences of the respective modules explained in the aforesaid exemplary embodiment such as the reference image extraction module 120, the reference image peripheral density extraction module 130, the feature data conversion module 140, the feature data/peripheral data register module 150, the peculiar feature data extraction module 170, the peculiar feature data register module 180, the reference image extraction module 220, the reference image peripheral density extraction module 230, the feature data conversion module 240, the collation (A) module 250, the peculiar feature data extraction module 270, the collation (B) module 280, the output module 290.

A ROM (Read Only Memory) 1902 stores the programs and operation parameters etc. used by the CPU 1901. A RAM (Random Access Memory) 1903 stores programs used at the time of the execution of the CPU 1901 and parameters etc. which suitably change at the time of the execution. These constituent elements are mutually coupled via a host bus 1904 configured by a CPU bus etc.

The host bus 1904 is coupled to an external bus 1906 such as a PCI (Peripheral Component Interconnect/Interface) bus via a bridge 1905.

Each of a key board 1908 and a pointing device 1909 such as a mouse is an input device operated by a user. A display 1910 is a liquid crystal device or a CRT (Cathode Ray Tube) and displays various kinds of information as texts and image information.

An HDD (Hard Disk Drive) 1911 contains hard disks and records and reproduces the programs and information executed by the CPU 1901 buy driving the hard disks. The hard disks store the target images, feature data, peripheral data, peculiar feature data etc. and also store various kinds of computer programs such as various kinds of data processing programs.

A driver 1912 reads data or program stored in a removable recording medium 1913 such as a magnetic disk, an optical disk, an magneto-optical disk or a semiconductor memory attached thereto and supplies the data or the program to the RAM 1903 which is coupled via an interface 1907, the external bus 1906, the bridge 1905 and the host bus 1904. The removable recording medium 1913 can also be used as a data recording area equivalent to the hard disk.

A coupling port 1914 is a port for connecting an external coupling device 1915 and has a coupling portion such as USB, IEEE1394. The coupling port 1914 is coupled to the CPU 1901 etc. via the interface 1907, the external bus 1906, the bridge 1905, the host bus 1904 etc. A communication portion 1916 is coupled to the network and executes a data communication processing with the external unit. The data reading portion 1917 is configured by a scanner, for example, and executes a reading processing of documents. The data output portion 1918 is configured by a printer, for example, and executes an output processing of document data.

FIG. 19 shows an example of the hardware configuration of the image processing apparatus (registering apparatus) and the image processing apparatus (collating apparatus) and the configuration of the exemplary embodiment is not limited thereto, and hence the configuration of the exemplary embodiment may be any one which can execute the respective modules explained in the aforesaid exemplary embodiment. For example, a part of the modules may be configured by a dedicated hardware (for example, an ASIC (Application Specific Integrated Circuit) etc.). Apart of the modules may be provided within an external system and connected via a communication line. Further, a plural sets of the system shown in FIG. 19 may be provided and coupled to each other via a communication line so as to operate in a cooperating manner. Further, the hardware configuration may be incorporated into a copy machine, a facsimile machine, a scanner, a printer, a complex machine (an image processing apparatus having the function of at least two of a scanner, a printer, a copy machine, a facsimile machine etc.).

Although in the aforesaid exemplary embodiment, the explanation is made as to the case where the object is mainly a tablet as an example, the object may be one other than a tablet.

The aforesaid exemplary embodiments may be combined (for example, the module within one of the exemplary embodiments is added into the other exemplary embodiment, or the modules of the exemplary embodiments are exchanged therebetween). Further, the technique explained in the background technique may be employed in the processing contents of the respective modules.

The programs explained above may be provided in a manner of being stored in a recording medium or via a communication means. In this case, for example, the invention of the program may be understood as the invention of "a computer readable recording medium in which the programs is recorded".

The "computer readable recording medium in which the programs is recorded" is a recording medium capable of being read by a computer used for installing, executing and distributing the programs, for example.

The recording medium may be, for example, a digital versatile disk (DVD) such as "DVD-R, DVD-RW, DVD-RAM etc." which is the standard formulated in the DVD forum or "DVD+R, DVD+RW etc." which is the standard formulated in the DVD+RW forum, a compact disk (CD) such as a read only memory (CD-ROM), a CD recordable (CD-R), a CD rewritable (CD-RW), a blue-ray disk (trademark), a magneto-optical disk (MO), a flexible disk (FD), a magnetic tape, a hard disk, a read only memory (ROM), an electrically erasable programmable read-only memory (EEPROM: trademark), a flash memory, a random access memory (RAM).

The programs or a part thereof may be recorded and stored in the recording medium and may be distributed, for example.

Further, the programs or a part thereof may be transmitted via the transmission medium such as the cable network or the wireless communication network or the combination thereof used in the local area network (LAN), the metropolitan area network (MAN), the wide area network (WAN), the internet, the intranet, the extranet etc. Alternatively, the programs or a part thereof may be transmitted by being superimposed on the carrier wave.

Further, one of the programs may be a part of another program and may be recorded in the recording medium together with another program. Further, the programs may be recorded into a plurality of the recording mediums in a divided manner. Furthermore, the programs may be recorded in any mode such as the compression or encryption so long as the programs can be restored.

The foregoing description of the exemplary embodiment of the present invention has been provided for the purpose of illustration and description. It is not intended to be exhaustive or to limit the invention to the precise forms disclosed. Obviously, many modifications and various will be apparent to practitioners skilled in the art. The embodiments were chosen and described in order to best explain the principles of the invention and its practical application, thereby enabling other skilled in the art to understand the invention for various embodiments and with the various modifications as are suited to the particular use contemplated. It is intended that the scope of the invention be defined by the following claims and their equivalents.

EXPLANATION OF SIGNS

100 image processing apparatus (registering apparatus)
110 image acquisition module
120 reference image extraction module
130 reference image peripheral density extraction module
140 feature data conversion module
150 feature data/peripheral data register module
160 feature data/peripheral data storage module
170 peculiar feature data extraction module
180 peculiar feature data register module
190 peculiar feature data storage module
200 image processing apparatus (collating apparatus)
210 image acquisition module
220 reference image extraction module
230 reference image peripheral density extraction module
240 feature data conversion module
250 collation (A) module
270 peculiar feature data extraction module
280 collation (B) module
290 output module

What is claimed is:

1. An image processing system comprising:
 a first image processing apparatus; and
 a second image processing apparatus,
 wherein the first image processing apparatus includes:
 at least one processor which executes:
 a first image obtaining module that obtains an image of an object having a seal impressed on a face thereof and having a film formed or laminated on the face thereof;
 a first image extraction module that extracts a partial image of the seal within the image obtained by the first image obtaining module;
 a first density extraction module that extracts a density of the partial image of the seal extracted by the first image extraction module;
 a first feature conversion module that converts a density sequence formed by a sequence of the densities extracted by the first density extraction module into a feature of the partial image of the seal; and a register module that registers the features converted by the first feature conversion module and the densities extracted by the first density extraction module into storage module so that the features and the densities are associated with each other, and the second image processing apparatus includes:

at least one processor which executes:

a second image obtaining module that obtains an image of an object having a seal impressed on a face thereof and having a film formed or laminated on the face thereof;

a second image extraction module that extracts a partial image of the seal within the image obtained by the second image obtaining module;

a second density extraction module that extracts a density of the partial image of the seal extracted by the second image extraction module;

a second feature conversion module that converts a density sequence formed by a sequence of the densities extracted by the second density extraction module into a feature of the partial image of the seal; and a collation module that extracts a density corresponding to the feature converted by the second feature conversion module from the storage module and performs collation between the extracted density and the density extracted by the second density extraction module, wherein the object comprises a tablet of medicine.

2. An image processing apparatus comprising:

a memory; and at least one processor which to execute:

an image obtaining module that obtains an image of an object having a seal impressed on a face thereof and having a film formed or laminated on the face thereof;

an image extraction module that extracts a partial image of the seal within the image obtained by the image obtaining module;

a density extraction module that extracts a density of the partial image of the seal extracted by the image extraction module;

a feature conversion module that converts a density sequence formed by a sequence of the densities extracted by the density extraction module into a feature of the partial image of the seal; and a register module that registers the features converted by the feature conversion module and the densities extracted by the density extraction module into storage module so that the features and the densities are associated with each other, wherein the object comprises a tablet of medicine.

3. The image processing apparatus according to claim 2 further comprising:

a second image extraction module that extracts an image at a predetermined position from a position of the partial image of the seal extracted by the image extraction module; and a second storage module that stores the image extracted by the second image extraction module into second storage module.

4. The image processing apparatus according to claim 2, wherein the image extraction module extracts an image within the image of the seal, as the partial image, in which an entire length of a continuous line has a predetermined value or more and a curved portion thereof has a predetermined length or more.

5. The image processing apparatus according to claim 2, wherein the image extraction module extracts an image of the seal located at a curved face of the object as the partial image when the object has a three-dimensional shape.

6. An image processing apparatus comprising:

a memory; and at least one processor which to execute:

an image obtaining module that obtains an image of an object having a seal impressed on a face thereof and also having a film formed or laminated on the face thereof;

an image extraction module that extracts a partial image corresponding to the seal within the image obtained by the image obtaining module;

a density extraction module that extracts a density of the partial image of the seal extracted by the image extraction module;

a feature conversion module that converts a density sequence formed by a sequence of the densities extracted by the density extraction module into a feature of the partial image of the seal; and a collation module that extracts a density corresponding to the feature converted by the feature conversion module from storage module in which features of partial images of a seal as a reference and densities of the partial images of the seal are registered in a corresponding manner respectively and performs collation between the extracted density and the density extracted by the density extraction module, wherein the object comprises a tablet of medicine.

7. The image processing apparatus according to claim 6 further comprising:

a second image extraction module that extracts an image at a predetermined position from a position of the partial image of the seal extracted by the image extraction module; and a second collation module that extracts the image from the second storage module claimed in claim 3 and collates the extracted image with the image extracted by the second image extraction module.

8. The image processing apparatus according to claim 6, wherein the image extraction module extracts an image within the image of the seal, as the partial image, in which an entire length of a continuous line has a predetermined value or more and a curved portion thereof has a predetermined length or more.

9. The image processing apparatus according to claim 6, wherein the image extraction module extracts an image of the seal located at a curved face of the object as the partial image when the object has a three-dimensional shape.

10. The image processing apparatus according to claim 6, wherein the image obtaining module obtains a plurality of images having respectively different inclination angles of the object by changing inclination of the object, and wherein the image obtaining module generates an image from the plurality of images thus obtained or each of the image extraction module, the density extraction module, the feature conversion module and the collation module performs a processing as to the plurality of images obtained by the image obtaining module.

11. A non-transitory computer readable medium storing a program causing a computer to execute a process for image processing, the process comprising:

obtaining an image of an object having a seal impressed on a face thereof and having a film formed or laminated on the face thereof;

extracting a partial image of the seal within the image obtained in the obtaining step;

extracting a density of the partial image of the seal extracted in the image extracting step;

converting a density sequence formed by a sequence of the densities extracted in the density extracting step into a feature of the partial image of the seal; and registering the features converted in the converting step and the densities extracted in the extracting step into storage module so that the features and the densities are associated with each other, wherein the object comprises a tablet of medicine.

12. A non-transitory computer readable medium storing a program causing a computer to execute a process for image processing, the process comprising:

obtaining an image of an object having a seal impressed on a face thereof and also having a film formed or laminated on the face thereof;

extracting a partial image corresponding to the seal within the image obtained in the image obtaining step;

extracting a density of the partial image of the seal extracted in the image extracting step;

converting a density sequence formed by a sequence of the densities extracted in the density extracting step into a feature of the partial image of the seal; and extracting a density corresponding to the feature converted in the feature conversion step from storage module in which features of partial images of a seal as a reference and densities of the partial images of the seal are registered;

performing collation between the extracted density and the density extracted in the density extraction step, wherein the object comprises a tablet of medicine.

* * * * *